Figure 1:
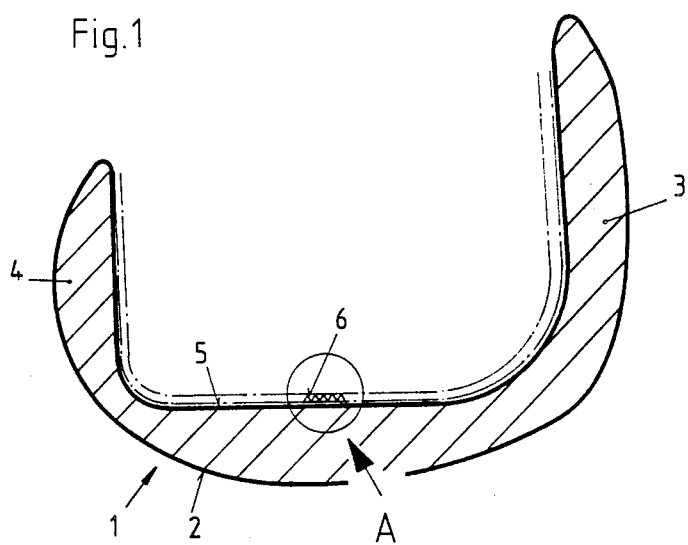

United States Patent [19]

Koch et al.

[11] Patent Number: 4,969,907
[45] Date of Patent: Nov. 13, 1990

[54] METAL BONE IMPLANT

[75] Inventors: Rudolf Koch, Berlingen; Otto Frey, Winterthur, both of Switzerland

[73] Assignee: Sulzer Brothers Limited, Winterthur, Switzerland

[21] Appl. No.: 803,715

[22] Filed: Dec. 2, 1985

[30] Foreign Application Priority Data

Jan. 8, 1985 [CH] Switzerland .............................. 61/85

[51] Int. Cl.⁵ ........................... A61F 2/38; A61F 2/28
[52] U.S. Cl. ......................................... 623/20; 623/16
[58] Field of Search ................... 623/20, 16; 427/125, 427/35

[56] References Cited

U.S. PATENT DOCUMENTS

| | | | |
|---|---|---|---|
| 4,038,703 | 8/1977 | Bokros | 623/20 X |
| 4,355,429 | 10/1982 | Mittelmeier et al. | 623/20 |
| 4,400,408 | 8/1983 | Asano et al. | 427/125 X |
| 4,542,539 | 9/1985 | Rowe, Jr. et al. | 623/20 X |

*Primary Examiner*—Alan W. Cannon
*Attorney, Agent, or Firm*—Kenyon and Kenyon

[57] ABSTRACT

The bone implant is made of a cobalt-based alloy and can be anchored to a bone through the accretion of tissue. The tissue friendly surface of the implant is provided by a coating and a structural element which is secured to the coating with each of the coating and structural element being made of titanium, tantalum or niobium or an alloy of one or more of these materials.

12 Claims, 1 Drawing Sheet

U.S. Patent    Nov. 13, 1990    4,969,907

METAL BONE IMPLANT

This invention relates to a metal bone implant. More particularly, this invention relates to a knee joint prosthesis.

As is known, many types of metal bone implants have been known for implanting in a body. For example, various types of metal bone implants have been used as knee joint endoprostheses wherein at least a part of one surface serves as a slide bearing surface while another surface is exposed for the accretion of tissue. Usually, these endoprostheses have been made of a material such as a cobalt-based cast alloy.

As is known, in articular endoprosthetics, cobalt based alloys are preferred for bone implants because of their good technical and mechanical properties, for example, their strength and their sliding properties. If such implants are to be fixed in a bone without interposition of a bone cement bed, that is, by accretion or ingrowth of tissue, difficulties arise in the adhesion between the bone and the implant. Because the cobalt based alloys do not have a tissue-friendly "behavior" the accretion of tissue occurs only with great difficulty.

Accordingly, it is an object of the invention to provide a bone implant which has an improved anchoring characteristic for cementless implantation.

It is another object of the invention to provide a bone implant made of a cobalt-based cast alloy which is tissue friendly.

It is another object of the invention to improve the adhesion characteristics of a cobalt-based cast alloy bone implant.

It is another object of the invention to provide a bone implant having improved tissue implant characteristics.

Briefly, the invention provides a bone implant which is comprised of a body having a surface which is exposed for the accretion of tissue, a metal coating on the surface which is selected from the group consisting of titanium, tantalum, niobium or an alloy thereof, and a structural element which is secured to the coating and which is made of a similar metal.

The use of a coating and a structural element made of the indicated materials offer to an ingrowing and accreting bone "partners" a definite tissue-friendly surface on or in which the bone grows or accretes especially well.

A firmly adhering coating of the above-mentioned tissue friendly materials can be readily formed on the implant body. For example, where the implant body is made of a cobalt-based cast alloy, the tissue friendly coating can be precipitated on the body by known methods, such as electroplating, vapor deposition, or flame or plasma spraying.

Preferably, the coating is of a thickness of at least 0.05 millimeters (mm).

The structural element which is secured to the coating may be in the manner of a corrugated sheet, for example as described in German O.S. No. 3416471, a metal grid, for example as described in European Patent Application No. 038902 or German A.S. No. 2404214, or a wire mesh, for example as described in German O.S. No. 3036520. In addition, the structural element may be stacked up in several layers for the ingrowth of tissues.

Advantageous, although not absolutely necessary, the structural element may be made of the same material, or at least contain the same base material, as the coating.

In order to improve the securement of the structural element to the coating, the structural element may be secured to the coating through punctiform metallurgical contact points produced, for example by spot welding. Such metallurgical contact points provide a good adhesion without having to expose the substrate or foundation material of the implant body to thermal loads which might alter the structure or reduce the desired mechanical properties of the implant body.

Figure 2:
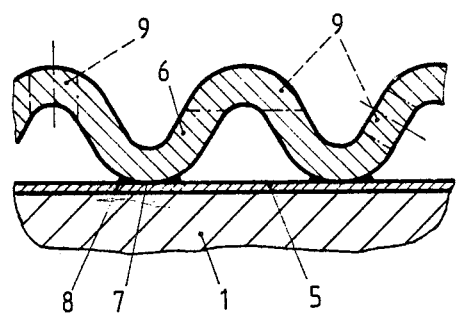

These and other objects and advantages of the invention will become more apparent from the following detailed description taken in conjunction with the accompanying drawings wherein:

FIG. 1 illustrates a cross sectional side view of a knee joint prosthesis for a femur condyle; and FIG. 2 illustrates an enlarged view of a detail of FIG. 1.

Referring to FIG. 1, the bone implant is constructed for use as a knee joint endoprosthesis, for example as a femur condyle prosthesis. The prosthesis includes a U-shaped body 1 having an outer surface which follows the form and dimensions of a natural femur condyle and which is made of a cobalt based cast alloy. In addition, the body has a polished bearing surface 2 which is intended to bear on and move relative to a corresponding counter-surface of a tibia part (not shown). Generally, the counter-surface is formed of a plastic, for example polyethylene.

The body 1 includes a shield 3 which is situated in the anterior direction and which serves as a sliding surface for a natural or artificial patella as well as a rear condylar arc 4. The body 1 thus defines an interior surface for exposure to an accretion of tissue such that the body may be fixed without cement in a kind of clamping fit on a femur bone (not shown). As such, the interior surface of the body 1 is in direct contact with the bone tissue.

The implant is provided with a coating 5 and a structural element 6 on the inside surface in order to ensure a firm seating of the prosthesis in as intimate as possible a connection between the bone (not shown) and the prosthesis body 1.

Referring to FIG. 2, the coating 5 is formed, for example of pure titanium. Alternatively, the coating may also be made of tantalum, niobium or an alloy of titanium, tantalum or niobium. In addition, the coating may be formed by a flame or plasma spray technique or any other suitable technique, to a thickness of from 0.05 to 1.0 millimeters (mm).

The structural element may be in the form of a corrugated sheet metal plate which is secured to the coating 5 in a number of bearing points 7, for example punctiform metallurgical contact points, by means of local welds 8. The structural element 6 is also made of pure titanium with a thickness, for example of 1.0 millimeters (mm). The structural element may also be made of tantalum, niobium or an alloy of titanium, tantalum or niobium. As indicated in FIG. 2, the structural element 6 may be provided with a plurality of openings 9, for example in the flanks and/or wave crests, for the ingrowth of tissue. To this end, the minimal dimensions of the cross section of the openings 9 should be at least 0.1 millimeter (mm).

The invention thus provides a bone implant which has a tissue-friendly surface into which tissue may accrete while the body of the implant is made of a cobalt-based alloy.

The invention further provides a bone implant which can be made of a cobalt-based alloy to have improved mechanical properties and sliding characteristics while at the same time having a surface which is tissue-friendly for the accretion of tissue in a cementless implantation.

What is claimed is:

1. A metal bone implant comprising
a body of a cobalt-based cast alloy having a bearing surface and a second surface for exposure to an accretion of tissue;
a tissue-friendly metal coating on said second surface selected from the group consisting of titanium, tantalum, niobium and alloys thereof; and
a structural element secured to said coating and being of a tissue-friendly metal selected from the group consisting of titanium, tantalum, niobium and alloys thereof.

2. A metal bone implant as set forth in claim 1 wherein said coating has a thickness of at least 0.05 millimeters.

3. A metal bone implant as set forth in claim 2 wherein said structural element is secured to said coating through punctiform metallurgical contact points.

4. A metal bone implant as set forth in claim 1 wherein said structural element is secured to said coating through punctiform metallurgical contact points.

5. A bone implant comprising
a body of a cobalt-based cast alloy having a surface for exposure to an accretion of tissue;
a tissue-friendly metal coating on said surface selected from the group consisting of titanium, tantalum, niobium and alloys thereof; and
a structural element secured to said coating and being of a tissue-friendly metal selected from the group consisting of titanium, tantalum, niobium and alloys thereof.

6. A bone implant as set forth in claim 5 wherein said coating has a thickness of at least 0.05 millimeters.

7. A bone implant as set forth in claim 5 wherein said structural element is welded to said coating.

8. A bone implant as set forth in claim 5 wherein said structural element has a plurality of openings therein for an ingrowth of tissue.

9. A bone implant as set forth in claim 8 wherein said openings have a minimum dimension of 0.1 millimeter.

10. A knee joint endoprosthesis comprising
a U-shaped body of a cobalt-based alloy having an outer bearing surface;
a tissue-friendly metal coating on an inner surface of said body; and
a tissue-friendly metal structural element secured to said coating for the accretion of tissue therein.

11. A knee joint prosthesis as set forth in claim 10 wherein each said coating and said structural element is of a metal selected from the group consisting of titanium, tantalum, niobium and alloys thereof.

12. A knee joint prosthesis as set forth in claim 10 wherein said structural element has a plurality of openings therein for an ingrowth of tissue.

* * * * *